United States Patent [19]

Yau

[11] Patent Number: 5,210,264

[45] Date of Patent: May 11, 1993

[54] S-(2,4-DICHLOROBENZYL)-B-CYANO-ETHYL PHOSPHOROTHIOATE DIESTER

[75] Inventor: Eric K. Yau, Kirkland, Wash.

[73] Assignee: ISIS Pharmaceuticals, Inc., Carlsbad, Calif.

[21] Appl. No.: 818,928

[22] Filed: Jan. 10, 1992

[51] Int. Cl.$^5$ ............... C01B 25/00; C01B 25/14
[52] U.S. Cl. ................. 558/167; 558/70; 536/25.33; 536/25.31; 536/23.1
[58] Field of Search ......... 536/27; 568/14; 558/70, 558/167

[56] References Cited

U.S. PATENT DOCUMENTS

| 3,687,808 | 8/1972 | Merigan et al. | 195/28 |
| 4,393,010 | 7/1983 | Crea | 558/167 |
| 4,517,338 | 5/1985 | Urdea et al. | 525/54.11 |
| 4,672,110 | 6/1987 | Letsinger | 536/27 |

FOREIGN PATENT DOCUMENTS

PCTUS9100-243  1/1991  PCT Int'l Appl.

OTHER PUBLICATIONS

Cohen, Oligodeoxynucleotides: Antisense Inhibitors of Gene Expression, CRC Press, Inc., Boca Raton, Fla., 1989.
Brill, J. Am. Chem. Soc., 111:2321, 1989.
Letsinger, J. Am. Chem. Soc., 98:3655, 1976.
Matteucci, J. Chem. Soc., 103:3185, 1981.
Brill, J. Am. Chem. Soc., 113:3972, 1991.
Yau et al., Tetrahedron Letters 31:1953, 1990.
Miller, Anti-cancer Drug Design, 2:117-128, 1987.
Daub, J. Am. Chem. Soc., 98:3526, 1976.
Matteucci, Bull. Chem. Soc., Jpn 60:1407, 1987.
Dahl, O. Sulfur Reports 11(1):167-192, 1991.
Eckstein, F. Ann. Rev. Biochem. 54:367-402, 1985.
Kresse et al. Nucl. Acids Res. 2(1):1-9, 1975.
Sekine et al. J. Org. Chem. 44(13):2325-2326, 1979.
Derwent Abstract No. 84-304546149. Daiichi Seiyaku KK, J5 9190-997-A, Oct. 29, 1984.

*Primary Examiner*—Brown Johnnie R.
*Assistant Examiner*—Gary L. Kunz
*Attorney, Agent, or Firm*—Woodcock Washburn Kurtz Mackiewicz & Norris

[57] ABSTRACT

The compound S-(2,4-dichlorobenzyl)-B-cyanoethyl phosphorothioate diester is disclosed as useful in the synthesis of phosphorothioate oligonucleotides. In certain embodiments of the invention, this reagent is used to prepare 3'-S-(alkaryl) phosphorothioates. The $\beta$-cyanoethyl blocking group can be removed and the resulting diester reacted with a nucleotide having a free 5'-hydroxyl group to yield compounds of the structure:

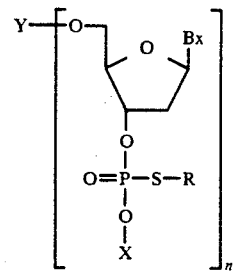

where X is H, a first blocking group, a nucleoside, a nucleotide or an oligonucleotide; Y is H, a second blocking group, a nucleotide or an oligonucleotide; R is an alkaryl or aryl group; n is an integer greater than 0; and Bx is a heterocyclic base. Deblocking of the S-alkaryl or S-aryl moiety yields a phosphorothioate oligonucleotide.

1 Claim, No Drawings

S-(2,4-DICHLOROBENZYL)-B-CYANOETHYL PHOSPHOROTHIOATE DIESTER

BACKGROUND OF THE INVENTION

This application is directed to a process for preparing phosphorothioate oligonucleotides and to intermediates used in that process. Nucleoside precursors are phosphitylated with S-(alkaryl or aryl) alkyl phosphorothioate diester salts and then reacted in solution phase to build phosphorothioate oligonucleotides.

It is well known that most of the bodily states in mammals including most disease states, are effected by proteins. Such proteins, either acting directly or through their enzymatic functions, contribute in major proportion to many diseases in animals and man. Classical therapeutics has generally focused upon interactions with such proteins in an effort to moderate their disease causing or disease potentiating functions. Recently, however, antisense methodology has been introduced to moderate the actual production of such proteins by interactions with messenger RNA (mRNA) or other intracellular RNA's that direct protein synthesis or with DNA's that direct the production of RNA. It is a general object of such therapeutic approaches to interfere with or otherwise modulate the expression of genes associated with undesired protein formation.

Antisense methodology is the complementary hybridization of relatively short oligonucleotides to single-stranded RNA or single-stranded DNA such that the normal, essential functions of these intracellular nucleic acids are disrupted. Hybridization involves sequence specific hydrogen bonding via Watson-Crick base pairs of the heterocyclic bases of oligonucleotides to RNA or DNA. Such base pairs are said to be complementary to one another.

Events that provide for the disruption of the nucleic acid function, as discussed by Cohen in *Oligonucleotides: Antisense Inhibitors of Gene Expression*, CRC Press, Inc., Boca Raton, Fla. (1989), are thought to include at least two types. The first is hybridization arrest. This denotes a terminating event in which an oligonucleotide inhibitor binds to the target nucleic acid and thus prevents, by simple steric hindrance, the binding of essential proteins, most often ribosomes, to the nucleic acid. Methyl phosphonate oligonucleotides such as disclosed by Miller, P. S. and Ts'O, P. O. P. (1987) *Anti-Cancer Drug Design*, 2:117-128, and α-anomer oligonucleotides are the two most extensively studied antisense agents that are thought to disrupt nucleic acid function by hybridization arrest.

In determining the extent of hybridization arrest of an oligonucleotide, the relative ability of an oligonucleotide to bind to complementary nucleic acids may be compared by determining the melting temperature of a particular hybridization complex. The melting temperature ($T_m$), a characteristic physical property of double helixes, denotes the temperature in degrees centigrade at which 50% helical (hybridized) versus coil (unhybridized) forms are present. $T_m$ is measured by using the UV spectrum to determine the formation and breakdown (melting) of hybridization. Base stacking, which occurs during hybridization, is accompanied by a reduction in UV absorption (hypochromicity). Consequently, a reduction in UV absorption indicates a higher $T_m$. The higher the $T_m$, the greater the strength of the binding of the strands. Non-Watson-Crick base pairing, i.e. base mismatch, has a strong destabilizing effect seen as a decrease in $T_m$.

A second type of terminating event for antisense oligonucleotides involves the enzymatic cleavage of the targeted RNA by intracellular RNase H. The mechanism of RNase H cleavages requires the hybridization of a 2'-deoxyribofuranosyl oligonucleotide to a targeted RNA. The resulting DNA-RNA duplex activates the RNase H enzyme. The activated enzyme cleaves the RNA strand. Cleavage of the RNA strand destroys the normal function of the RNA. Phosphorothioate oligonucleotides are one prominent example of antisense agents that operate by this type of antisense terminating event.

The current method of choice for the preparation of phosphorothioate oligonucleotides is via solid-phase synthesis wherein an oligonucleotide is prepared on a polymer support. Solid-phase synthesis relies on sequential addition of nucleotides to one end of a growing oligonucleotide. Typically, a first nucleoside is attached to an appropriate glass bead support and nucleotide phosphoramidites are added stepwise to elongate the growing oligonucleotide. The nucleotide phosphoramidites are reacted with the growing oligonucleotide using the principles of a "fluidized bed" for mixing of the reagents. The known silica supports suitable for anchoring the oligonucleotide are very fragile and thus can not be exposed to aggressive mixing. Brill, W. K.-D., Tang, J.-Y., Ma, Y.-Y. and Caruthers, M. H. (1989) *J. Am. Chem. Soc.*, 111: 2321 disclosed a procedure wherein an aryl mercaptan is substituted for the nucleotide phosphoramidite to prepare phosphorodithioate oligonucleotides on glass supports.

In these and other solid-phase procedures the oligonucleotide is synthesized as an elongating strand. However, the number of individual strands that can be anchored to a unit surface area of the support is limited. Also, the activated nucleotides that are added to the growing oligonucleotide are relatively expensive and must be used in stoichiometric excess.

While presently-utilized solid-phase syntheses are very useful for preparing small quantities of oligonucleotide, i.e., up to about 0.4 mole per synthetic run, they typically are not amenable to the preparation of the larger quantities of oligonucleotides necessary for biophysical studies, pre-clinical and clinical trials and commercial production. A general review of solid-phase verse solution-phase oligonucleotide synthesis is given in the background section of U.S. Pat. No. 4,517,338, entitled Multiple Reactor System And Method For Polynucleotide Synthesis, to Urdea, et al.

Solution-phase synthetic oligonucleotide techniques should be useful for large scale preparation. One such solution phase preparation utilizes phosphorus triesters. As I reported [Yau, E. K., Ma, Y.-S. and Caruthers (1990) *Tetrahedron Letters*, 31:1953], the triester oligonucleotide approach can be utilized to prepare thymidine dinucleoside and thymidine dinucleotide phosphorodithioates. The phosphorylated thymidine nucleoside intermediates utilized in this approach were obtained by treatment of commercially available 5'-O-dimethoxytritylthymidine-3'-[(β-cyanoethyl)-N,N-diisopropyl]-phosphoramidite first with either 4-chloro or 2,4-dichlorobenzylmercaptan and tetrazole and then a saturated sulfur solution. The resulting phosphorodithioate nucleotide was then reacted via the triester synthesis method with a further thymidine nucleoside having a free 5'-hydroxyl.

Brill, W. K.-D., Nielsen, J. and Caruthers, M. H. (1991) *J. Am. Chem. Soc.*, 113:3972, recently disclosed that treatment of a phosphoramidite such as N,N-diisopropyl phosphoramidite with a mercaptan such as 4-chloro or 2,4-dichlorobenzylmercaptan in the presence of tetrazole yields a derivative suitable for preparation of a phosphorodithioate as a major product and a derivative suitable for preparation of a phosphorothioate as a minor product. Substituting 4-chloro or 2,4-dichlorobenzylmercaptan for N,N-diisopropyl phosphoramidite therefore would be expected to result in low yields of phosphorothioate oligonucleotides.

Thus, although the utility of phosphorothioate oligonucleotides in antisense methodology has been recognized, the art suggests no large scale techniques for their preparation. Accordingly, there remains a long-felt need for such methods and for intermediates useful in such methods.

OBJECTS OF THE INVENTION

It is one object of this invention to provide new and improved oligonucleotide synthetic methods.

It is a further object to provide improved methods for the preparation of phosphorothioate oligonucleotides.

A still further object is to provide intermediates for preparing phosphorothioate oligonucleotides.

BRIEF DESCRIPTION OF THE INVENTION

In accordance with this invention there are provided processes for the preparation of phosphorothioate oligonucleotides. In certain embodiments, these processes include the steps of (a) reacting thiophosphoryl chloride (PSCl$_3$) with an alkaryl halide or an aryl halide to form a first reaction intermediate and then, (b) reacting the first reaction intermediate with a nucleoside having a 3'-hydroxyl moiety, a nucleotide having a 3'-hydroxyl moiety, or an oligonucleotide having a 3'-hydroxyl moiety to form a second reaction intermediate selected from a nucleoside 3'-S-(alkaryl or aryl) phosphorothioate, a nucleotide 3'-S-(alkaryl or aryl) phosphorothioate or an oligonucleotide 3'-S-(alkaryl or aryl) phosphorothioate. The second reaction intermediate then is, (c) reacted with a nucleoside having a free 5'-hydroxyl moiety, a nucleotide having a free 5'-hydroxyl moiety or an oligonucleotide having a free 5'-hydroxyl moiety in the presence of an activating agent to form an ester linkage between a S-(alkaryl or aryl) phosphorothioate moiety of said second reaction intermediate and said 5'-hydroxyl moiety.

Preferably these processes include the further steps of hydrolyzing the PSCl$_3$ prior to reacting the PSCl$_3$ with the alkaryl or aryl halide and reacting the hydrolyzed PSCl$_3$ with the alkaryl or aryl halide. Even more preferred processes include the further steps of reacting the PSCl$_3$ with an alkyl alcohol prior to hydrolysis to form an alkoxy intermediate and then hydrolyzing the alkoxy intermediate prior to reacting the hydrolyzed alkoxy intermediate with the alkaryl or aryl halide.

In preferred embodiments of the invention, the product of step (c) of the above-described process is reacted one or more times with one of a further nucleoside 3'-S-(alkaryl or aryl) phosphorothioate, nucleotide 3'-S-(alkaryl or aryl) phosphorothioate or oligonucleotide 3'-S-(alkaryl or aryl) phosphorothioate.

Further in accordance with this invention there are provided processes for the preparation of phosphorothioate internucleoside linkages. In certain embodiments, these processes include phosphitylating two 5'-blocked nucleosides with an S-(alkaryl or aryl) alkyl phosphorothioate diester salt followed by deblocking the 5'-blocking group from one of the phosphitylated nucleosides and dealkylating the other of the phosphitylated nucleosides. The dealkylated nucleoside is then reacted with the deblocked nucleoside to form a dinucleoside having an S-(alkaryl or aryl) phosphorothioate internucleoside linkage. In preferred embodiments, the S-(alkaryl or aryl) bond of the S-(alkaryl or aryl) phosphorothioate internucleoside linkage is cleaved to yield a dinucleoside having a phosphorothioate internucleoside linkage. 2,4-Dichlorobenzyl is preferred as the alkaryl or aryl moiety of the S-(alkaryl or aryl) alkyl phosphorothioate diester salt and β-cyanoethyl is preferred as the alkyl moiety of S-(alkaryl or aryl) alkyl phosphorothioate diester salt.

Further in accordance with this invention are provided compounds of the structure:

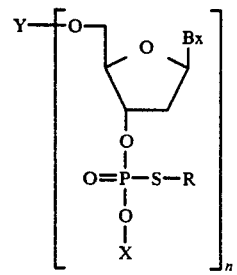

wherein:
X is H, a first blocking group, a nucleoside, a nucleotide or an oligonucleotide;
Y is H, a second blocking group, a nucleoside, a nucleotide or an oligonucleotide;
R is an alkaryl or aryl group;
n is an integer greater than 0; and
Bx is a heterocyclic base.

Further in accordance with this invention are provided compounds of the structure:

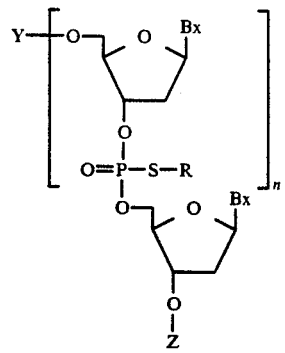

wherein:
X is H, a first blocking group, a nucleoside, a nucleotide or an oligonucleotide;
Y is H, a second blocking group, a nucleoside, a nucleotide or an oligonucleotide;

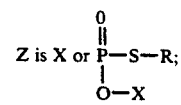

R is an alkaryl or aryl group;
n is an integer greater than 0; and
Bx is a heterocyclic base.

DETAILED DESCRIPTION OF THE INVENTION

This invention provides new and improved processes for the preparation of phosphorothioate oligonucleotides and for intermediates useful in these processes. Utilizing these processes and intermediates, phosphorothioate oligonucleotides are prepared from a plurality of phosphorothioate nucleotide subunits. The nucleotide subunits may be "natural" or "synthetic" moieties. Thus, in the context of this invention, the term "oligonucleotide" in a first instance refers to a polynucleotide formed from a plurality of joined nucleotide units. The nucleotides are joined via phosphorothioate internucleoside linkages. The nucleotides are formed from naturally occurring bases and pentofuranosyl sugar groups. The term "oligonucleotide" thus effectively includes naturally occurring species or synthetic species formed from naturally occurring subunits.

Oligonucleotides according to the invention also can include modified subunits. Representative modifications include modification of a heterocyclic base portion of a nucleotide or a sugar portion of a nucleotide. Exemplary modifications are disclosed in the following U.S. patent applications: Ser. No. 463,358, filed Jan. 11, 1990, entitled Compositions, And Methods For Detecting And Modulating RNA Activity now abandoned; Ser. No. 566,977, filed Aug. 13, 1990, entitled Sugar Modified Oligonucleotides That Detect And Modulate Gene Expression now abandoned; Ser. No. 558,663, filed Jul. 27, 1990, entitled Novel Polyamine Conjugated Oligonucleotides now U.S. Pat. No. 5,138,045 issued Aug. 11, 1991; Ser. No. 558,806, filed Jul. 27, 1991 now abandoned, entitled Nuclease Resistant Pyrimidine Modified Oligonucleotides That Detect And Modulate Gene Expression and Ser. No. PCT/US91/00243, filed Jan. 11, 1991, entitled Compositions and Methods For Detecting And Modulating RNA Activity. Each of these patent applications are assigned to the assignee of this invention. The disclosure of each is herein incorporated by reference.

The term oligonucleotide thus refers to structures that include modified portions, be they modified sugar moieties or modified base moieties, that function similarly to natural bases and natural sugars. Representative modified bases include deaza or aza purines and pyrimidines used in place of natural purine and pyrimidine bases; pyrimidines having substituent groups at the 5 or 6 position; purines having altered or replacement substituent groups at the 2, 6 or 8 positions. Representative modified sugars include carbocyclic or acyclic sugars, sugars having substituent groups at their 2' position, and sugars having substituents in place of one or more hydrogen atoms of the sugar. Other altered base moieties and altered sugar moieties are disclosed in U.S. Pat. No. 3,687,808 and PCT application PCT/US89/02323.

Altered base moieties or altered sugar moieties also include other modifications consistent with the spirit of this invention. Such oligonucleotides are best described as moieties that are structurally distinguishable from yet functionally interchangeable with naturally occurring or synthetic wild type oligonucleotides. All such oligonucleotides are comprehended by this invention so long as they function effectively to mimic the structure of a desired RNA or DNA strand.

For use in antisense methodology, the phosphorothioate oligonucleotides of the invention preferably comprise from about 10 to about 30 subunits. It is more preferred that such oligonucleotides comprise from about 15 to about 25 subunits. As will be appreciated, a subunit is a base and sugar combination suitably bound to adjacent subunits through a phosphorothioate linkage. When used as "building blocks" in assembling phosphorothioate oligonucleotides, even smaller assemblies are preferred. The smallest assembly is a phosphorothioate nucleotide having S-(alkaryl or aryl) and alkyl ester groups. The smallest dinucleoside assembly is two nucleosides linked by a protected phosphorothioate linkage.

It will be recognized that phosphorothioate oligonucleotides having tens or even hundreds of individual nucleotide subunits can be prepared utilizing the processes and intermediates of this invention. Such very large phosphorothioate oligonucleotides can be assembled from smaller oligonucleotide intermediates that, in turn, would be assembled from even smaller intermediates. Thus, phosphorothioate oligonucleotides and phosphorothioate oligonucleotide intermediates of the invention contain one or more subunits.

The phosphorothioate oligonucleotides of the invention can be used in diagnostics, therapeutics and as research reagents and kits. They can be used in pharmaceutical compositions by including a suitable pharmaceutically acceptable diluent or carrier. They further can be used for treating organisms having a disease characterized by the undesired production of a protein. The organism should be contacted with a phosphorothioate oligonucleotide having a sequence that is capable of specifically hybridizing with a strand of nucleic acid coding for the undesirable protein. Treatments of this type can be practiced one a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, since each cell of multicellular eukaryotes can be treated since they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic phosphorothioate oligonucleotides. As used herein, therapeutics is meant to include the eradication of a disease state, by killing an organism or by control of erratic or harmful cellular growth or expression.

In the process illustrated in Scheme 1, thiophosphoryl chloride ($PSCl_3$; structure 1) is treated with an alkyl alcohol such as cyanoethanol (structure 2) in the presence of a suitable HCl scavenger to yield a mixture of mono, di and tri alkylated phosphorothioate species (mixture 1; structures 3, 4 and 5). $C_1$ to $C_{10}$ alkyl alcohols are preferred. Even more preferred are alkyl alcohols comprising a substituent that can be activated to facilitate removal of the alkyl group. For example, cyanoethanol contains a cyanoethyl moiety that can be eliminated via a controlled β-elimination reaction. Other useful alkyl alcohols include electron withdrawing groups positioned on the alkyl chain such that reaction with PSCl$_3$ results in an acidic proton located on the carbon atom β to the phosphorus atom. Representative electron withdrawing groups include methyl groups [Daub, G. W. and van Tamelen, E. E. (1976) *J. Am. Chem. Soc.* 98:3526.], 2,2,2-trichloroethyl groups [Letsinger, R. L. and Lunsford, W. B. (1976) *J. Am. Chem. Soc.*, 98:3655] and trihalomethylethyls such as trichlordimethylethyl, trichloromethylethyl, tribromodimethylethyl, tribromomethylethyl and tribromoethyl [See, e.g., U.S. Pat. No. 4,672,110]. A preferred HCl scavenger is 2,6-lutidine, which facilitates the reactivity of the alkyl alcohol with the chloro substituents of the PSCl$_3$. Other useful HCl scavengers include diisopropylethylamine, 2-methylpyridine or other hindered tertiary amines.

Reaction of thiophosphoryl chloride with an alkyl alcohol such as cyanoethanol yields a mixture (mixture 1) of di-chloro-β-cyanoethyl phosphorothioate monoester (structure 3), chloro-di-(β-cyanoethyl) phosphorothioate diester (structure 4) and tri-β-cyanoethyl phosphorothioate triester (structure 5). In accordance with the invention, the chloro groups of structure 3 and structure 4 are then hydrolyzed. Also, one of the alkyl esters of structure 5 should be cleaved. For example, cyanoethyl esters can be cleaved via a β-elimination reaction to yield a further mixture (mixture 2) containing β-cyanoethyl phosphorothioate ester (structure 6) and di(β-cyanoethyl) phosphorothioate ester (structure 7). Preferably hydrolysis and cleavage are effected concurrently by treating mixture 1 with an aqueous tertiary alkylamine. Preferred tertiary alkylamines are trialkyl amines such as triethylamine and diisopropylethyl amine. The electron withdrawing effect of the cyano group is believed to result in abstraction by the tertiary alkyl amine of a cyanoethyl proton and elimination of the cyanoethyl ester. A 1:1 (volume:volume) mixture of 0.5M triethylamine buffer in acetonitrile is preferred.

Structures 3 and 4 can be hydrolyzed without cleavage of structure 5 by, for example, treating mixture 1 with an amine species that does not effect β-elimination. Unreacted structure 5 then can be removed from the hydrolysis product. It will be recognized, however, that the overall yields from such a procedure likely will be low.

While not wishing to be bound by any particular theory, it is believed that hydrolysis of the chloro moieties of structures 3 and 4 is more facile than the ester β-elimination in structure 5. Thus, treatment of mixture 1 with aqueous amine results in hydrolysis of the chloro groups before ester cleavage. It also is believed that the presence of an anionic charge on a phosphorothioate ester of mixture 1 or mixture 2 inhibits subsequent β-elimination of β-cyanoethyl esters.

Accordingly, the phosphorothioate moieties that result upon β-elimination of a first cyanoethyl ester group of structures 4 or 5 or upon hydrolysis of a chloro group of structures 3 or 4 have a single anionic charge. The presence of this charge inhibits β-elimination of β-cyanoethyl ester groups. As a result, structure 5 is cleaved to form a di-(β-cyanoethyl) phosphorothioate diester (structure 6). Structure 4 is hydrolyzed to this same compound and structure 3 is hydrolyzed to a β-cyanoethyl phosphorothioate monoester (structure 7). If ester elimination is more facile than hydrolysis, elimination of a first ester moiety from structure 4 would generate an anionic charge that, in turn, would inhibit elimination of the remaining ester group to form structure 7. Hydrolysis of a first chloro group of structure 3 is expected to be even more facile than hydrolysis of the single chloro group of structure 4. This would generate an anionic structure that would prevent elimination of the ester group of structure 3 prior to hydrolysis of the second chloro group. However, if ester elimination is more facile than hydrolysis of the first chloro group, elimination of the ester group of structure 3 followed by hydrolysis would generate phosphorothoic acid or phosphorothiolic acid. As shown in the experimental examples below, such acids would be easily removed during work up of the reactions mixtures.

In accordance with the invention, mixture 2 is then reacted with an alkaryl halide or an aryl halide (structure 8) such as a benzyl, substituted benzyl, phenyl or substituted phenyl halide. This results in the formation of an S-alkaryl or S-aryl ester, i.e. an S-benzyl ester or an S-phenyl ester. Esterification of the thio moieties of structures 6 and 7 with an aryl halide yields a mixture containing S-(alkaryl or aryl)-di-(β-cyanoethyl) phosphorothioate triester (not illustrated or numbered) and S-(alkaryl or aryl) β-cyanoethyl phosphorothioate diester (structure 9). Concurrent treatment with a tertiary alkylamine results in β-elimination of one of the cyanoethyl ester groups of the S-(alkaryl or aryl)-di-(β-cyanoethyl) phosphorothioate to provide an S-(alkaryl or aryl)-β-cyanoethyl phosphorothioate diester having structure 9. This S-(alkaryl or aryl) alkyl phosphorothioate diester salt has a single anionic charge and, thus, is inert to further β-elimination.

Structure 9 preferably is a triethyl ammonium salt, a diisopropylethyl ammonium salt, or a mixture thereof. Representative compounds having structure 9 include S-(4-chlorobenzyl)-β-cyanoethyl phosphorothioate diester salt, S-(2,4-dichlorophenyl)-β-cyanoethyl phosphorothioate diester salt, S-(2,4-dichlorophenyl)-β-cyanoethyl phosphorothioate diester salt and S-benzyl-β-cyanoethyl phosphorothioate diester salt. S-(2,4-dichlorobenzyl)-β-cyanoethyl phosphorothioate diester salt is preferred.

As shown in Scheme II, a salt having structure 9 can be used to directly phosphitylate a 3'-hydroxy nucleoside (structure 10) to produce a nucleoside S-(aryl) alkyl phosphorothioate triester (structure 11). For this phosphitylation reaction, the 5' hydroxyl group of the nucleoside is first blocked with a suitable blocking group (Y). Depending on the nucleoside, it also may be desirable to block the nucleoside on its heterocyclic base (Bx). For example, thymidine (or uracil if RNA nucleosides are utilized) need only be blocked at the 5' hydroxyl position, while cytidine and adenosine preferably also are blocked on their heterocyclic bases utilizing benzoyl blocking groups. Guanosine should be blocked at the 6-keto position of its heterocyclic base with a suitable keto blocking group including but not limited to diphenylcarbamate, isobutyryl (after first reacting with 1,2-glyoxal and including an additional isobutyryl group at the N2 position of the heterocyclic base in the manner of Matsuzaki, J., Kohno, K., Tahara, S., Sekine, M. and Hata, T. (1987) *Bull. Chem. Soc. Jpn.*, 60:1407), and β-eliminators such as cyanoethoxy groups. The guanosine nucleoside is then further blocked at the 5' hydroxyl.

A wide variety of nucleosides having general structure 10 can be incorporated into phosphorothioate oligonucleotides utilizing the process of the invention. Suitable nucleosides are disclosed in the patents, patent applications, and/or papers noted above.

The 5' hydroxyl blocking group Y can be selected from dimethoxytrityl (DMTr), methoxytrityl (MTr), trityl (Tr), tert-butyldimethylsilyl (TBDMSi), tert-butoxydiphenylsilyl (TBODPSi), dialkylphosphite, pivalylisobutyloxycarbonyl and other known hydroxyl blocking groups. Dimethoxytrityl and tert-butoxydiphenylsilyl groups are preferred. Generally, blocking group Y is selected to be base stable and acid labile. Deblocking of such groups usually can be effected with acids such as 3% trichloroacetic acid (3% TCA) or a Lewis acid such as $ZnBr_2$ or $TiCl_4$. See, e.g., Matteucci, M. D. and Caruthers, M. H. (1981) *J. Am. Chem. Soc.*, 103:3185]

Since the nucleoside of structure 11 does not bear an anionic charge, treatment with an amine removes the remaining $\beta$-cyanoethyl ester group on the phosphorothioate moiety to yield structure 12. Treatment of structure 11 with acid removes the 5' hydroxyl blocking group and yields structure 13, i.e. a phosphorothioated nucleoside having a free 5' hydroxyl group. For example, dimethoxytrityl blocking groups can be removed with either 3% trichloroacetic acid or $ZnBr_2$.

Compounds having structure 12 are then reacted with compounds having structure 13 as shown in Scheme III to yield dinucleotides having structure 14. Structure 14 bears blocking group Y on its 5' terminal hydroxyl and a $\beta$-cyanoethyl ester blocking group on its 3' terminal phosphorothioate. 3'-Terminal blocking groups are represented by the symbol X in certain structures of this specification.

Reaction of structures 12 and 13 is conducted in the presence of an activating agent. Preferred activating agents are disclosed by Yau, E. K., Ma, Y.-X. and Caruthers, M. H. (1990) *Tetrahedron Letters*, 31:1953. A particularly preferred activating agent is triisopropylbenzenesulfonylchloride (TPSCl), which normally is used in the presence of a nucleophilic catalyst such as 1-methylimidazole.

Dinucleotide structure 14 can be deblocked at its 3' terminal phosphorothioate to yield compounds of structure 15 and at its 5' terminal hydroxyl group to yield compounds of structure 16. Reaction of dinucleotide compounds having structures 15 and 16 in the presence of the activating agent will yield tetrameric oligonucleotides having structure 17, as shown in Scheme IV. Oligonucleotides having structure 17 can then be elongated using reactions analogous to those shown in Schemes II or III to effect the addition of nucleosides, phosphorothioate nucleotides, phosphorothioate dinucleotides or phosphorothioate oligonucleotides. These reactions should involve deblocking (deesterification) at a terminal 3' phosphorothioate and reaction in the presence of an activating agent with a further nucleoside, nucleotide or oligonucleotide having a free 5' terminal hydroxyl group.

Phosphodiester or other non-phosphorothioate nucleotides, dinucleotides or oligonucleotides can be added to the phosphorothioate oligonucleotide intermediates of this invention by reacting the non-phosphorothioate species with an activated phosphorothioate intermediate such as structure 12, structure 15, structure 17 or structure 22. To add a non-phosphorothioate species at a 3' terminus of a phosphorothioate intermediate, the non-phosphorothioate species should have a free 5' hydroxyl group that can form an ester linkage with the phosphorothioate intermediate or other like structure. To add a non-phosphorothioate species at the 5' terminus of a phosphorothioate intermediate, the non-phosphorothioate species should be added as an activated species to a phosphorothioate intermediate such as structure 13, structure 16 or structure 20 having a free 5' hydroxyl group.

Upon synthesis of a phosphorothioate oligonucleotide having a desired antisense or other sequence, the S-alkaryl or S-aryl blocking groups on the phosphorothioate linkages are removed. Deblocking of the S-alkaryl or S-aryl group preferably is effected utilizing thiophenolate in the manner described by Brill, W. K.-D., Nielsen, J. and Caruthers, M. H. (1991) *J. Am. Chem. Soc.*, 113 3972. Other deblocking conditions using thiophenol are described by Brill, W. K.-D., Tang, J.-T., Ma, Y.-X. and Caruthers, M. H. (1989) *J. Am. Chem. Soc.*, 111:2321.

In the following schemes Y is a blocking group, M is a metal salt, Bx is a heterocyclic base, TPSCl is triisopropylbenzenesulfonylchloride, MeIm is methylimidazole, TCA is trichloroacetic acid, THF is tetrahydrofuran, DMTr is dimethoxytrityl and OCE is cyanoethoxy.

SCHEME I

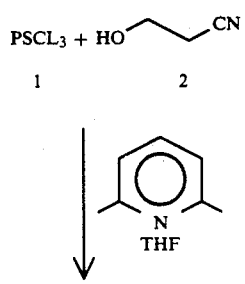

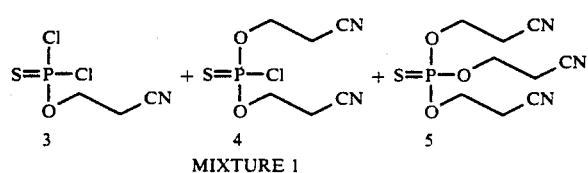
MIXTURE 1
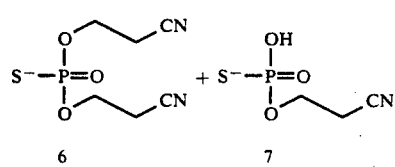
MIXTURE 2
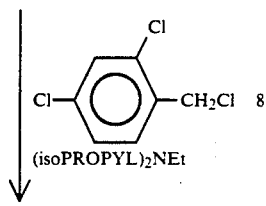
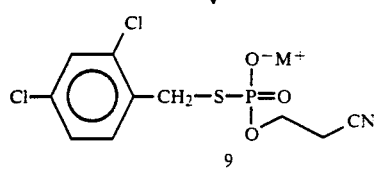
SCHEME II
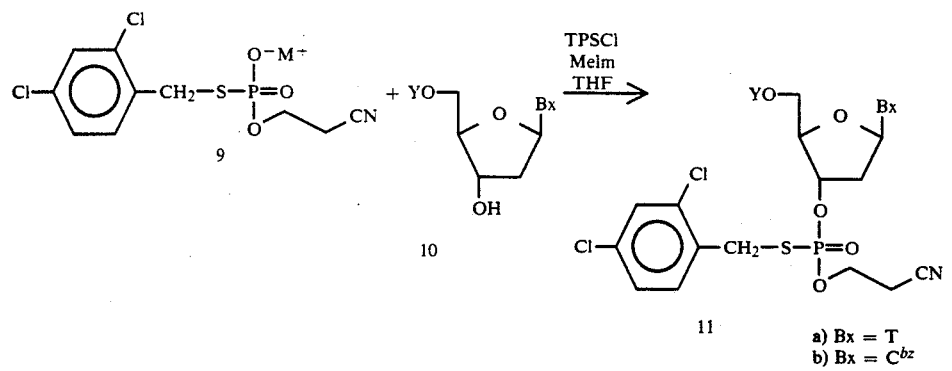
a) Bx = T
b) Bx = C$^{bz}$
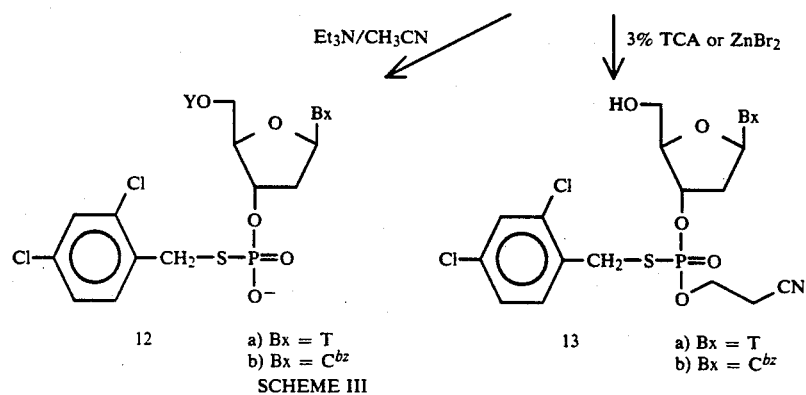
12  a) Bx = T
    b) Bx = C$^{bz}$
13  a) Bx = T
    b) Bx = C$^{bz}$
SCHEME III

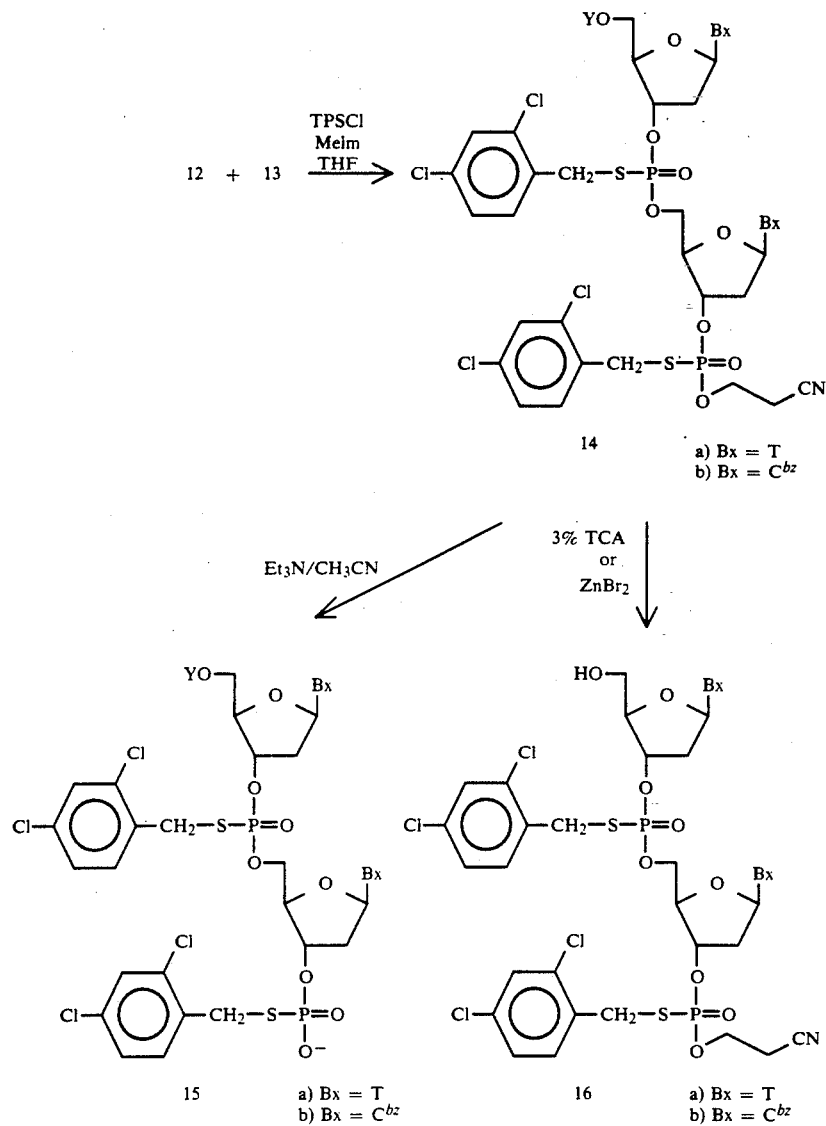
SCHEME IV
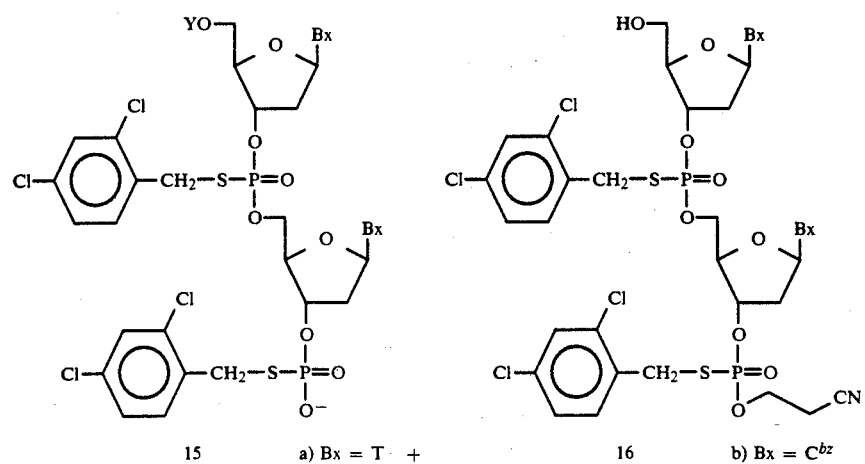

-continued $\downarrow$ TPSCl / MeIm / THF

DMTr-TTC$^{bz}$C$^{bz}$-OCE

17

$\downarrow$ 3% TCA

HO-TTC$^{bz}$C$^{bz}$-OCE

20

$\downarrow$ 19 + TPSCl / MeIm / THF

DMTr-ATTC$^{bz}$C$^{bz}$-OCE

21

$\downarrow$ Et$_3$N/CH$_3$CN

DMTr-ATTC$^{bz}$C$^{bz}$-O$^-$

22

$\downarrow$ 3'-O-Tr-2'-deoxyG + TPSCl / MeIm / THF

DMTr-ATTC$^{bz}$C$^{bz}$G-OTr

23

$\downarrow$ 3% TCA / thiophenolate

HO-ATTC$^{bz}$C$^{bz}$G-OH

24

The above-described procedures can be used to prepare oligonucleotides of the structure:

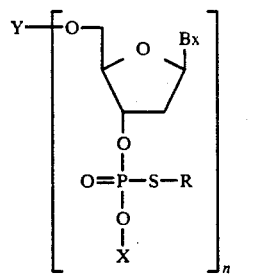

where X is H, a first blocking group, a nucleoside, a nucleotide or an oligonucleotide; Y is H, a second blocking group, a nucleoside, a nucleotide or an oligonucleotide; R is an alkaryl or aryl group; n is an integer greater than 0; and Bx is a heterocyclic base.

These procedures also can be used to prepare oligonucleotide of the structure:

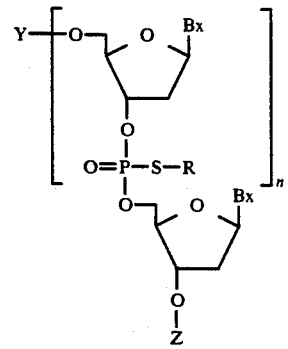

where X is H, a first blocking group, a nucleoside, a nucleotide or an oligonucleotide; Y is H, a second blocking group, a nucleoside, a nucleotide or an oligonucleotide;

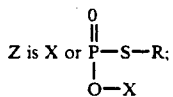

R is an aryl group; n is an integer greater than 0; and Bx is a heterocyclic base.

In each of these structures, heterocyclic base groups Bx of individual nucleosides or nucleotides can be the same or different. Bx preferably is a purin-9-yl or pyrimidin-1-yl base, more preferably adenine, guanine, cytosine, thymine, uracil, hypoxanthine, 2-aminoadenine or 5-methylcytosine.

Additional objects, advantages, and novel features of this invention will become apparent to those skilled in the art upon examination of the following examples thereof, which are not intended to be limiting.

EXAMPLES

Material and Methods. All reaction solvents were purified by known methods. The phrase "worked up in the usual manner" refers to washing the organic layer with saturated $NaHCO_3$, water and saturated brine, drying it over $Na_2SO_4$, filtering and evaporating to dryness. Solvent deoxygenation was accomplished by bubbling a stream of argon through the solvent during two freeze —thaw cycles using a dry ice/2-propanol bath. NMR proton spectra are reported as parts per million versus internal tetramethylsilane standards. Phosphorus resonances are reported relative to phosphoric acid.

EXAMPLE 1

S-(2,4-Dichlorobenzyl)-β-cyanoethyl phosphorothioate diester salt (9)

Method A

To a solution of 6.83 ml (7.11 g; 100 mmole) of 3-hydroxypropionitrile and 11.8 ml (10.7 g; 100 mmole) of 2,6-lutidine in 60 ml THF was added dropwise 5 ml (8.47 g; 50 mmole) of $PSCl_3$. The mixture was stirred a r.t. under argon for 3 days, at which time the precipitate was filtered off and washed with THF twice. The combined filtrate was concentrated in vacuo to give a crude intermediate. This intermediate was immediately treated with 600 ml of $CH_3CN$/0.5M triethylammonium bicarbonate buffer (PH 7.0) (1/1; v/v) at r.t. for 1 day. Solvent was removed in vacuo and the resulting residue was coevaporated once with $H_2O$/$Et_3N$ (9/1; v/v), twice with dry pyridine and then further dried under high vacuum overnight. The dried intermediate was dissolved in 200 ml DMF and 34 ml (25.2 g; 195 mmole) of diisopropylethylamine. To this solution was added 20.8 ml (29.3 g; 150 mmole) of α,2,4-trichlorotoluene. The reaction mixture was stirred at r.t. under argon for 1½ days, at which time the precipitate was removed by filtration and the filtrate was evaporated in vacuo. The obtaining residue was dissolved in $CH_2Cl_2$ and washed with $H_2O$ once. The $H_2O$ layer was back washed once with $CH_2Cl_2$ and the $CH_2Cl_2$ layers were combined, washed once with saturated NaCl, dried over $Na_2SO_4$, filtered and evaporated to give a crude syrup. This syrup was triturated with hexane (3×200 ml) and then purified by flash column on C-18 reverse phase silica gel (4:6 MeOH/$H_2O$). Fractions which contained the desired product (checked by UV at 230 & 240 nm and $^{31}$p-NMR) were pooled and concentrated. The syrupy product (9) (9.49 g) was obtained as a 9:1 mixture of the diisopropylethyl ammonium and triethyl ammonium salt forms, respectively. (42% yield based on $PSCl_3$) $^{31}$p-NMR ($CDCl_3$; ppm): 17.1. $^1$H-NMR ($CDCl_3$; δ): 7.51 (d, J=8.3 Hz, 1H, ArH), 7.35 (d, J=2.1 Hz, 1H, ArH), 7.18 (dd J=8.3 & 2.1 Hz, 1H, ArH), 4.00 (m, 4H, $SCH_2$ & $OCH_2$), 3.58 (m, 1.8H, CH), 3.04 (m, 2.4H, $CH_2$), 2.61 (t, J=6.4 Hz, 2H, $CH_2CN$), 1.40 (m, 14.4H, $CH_3$).

Method B

The procedure as described in A was followed except that $Et_3N$ was used instead diisopropylethyl amine in the last alkylation step to provide 77.8 g of (9) from 0.5 mole of $PSCl_3$. (36%) $^{31}$p-NMR showed the product in this preparation contained 2% phosphorus impurity and $^1$H-NMR showed it contained some aromatic impurity. However, these impurities did not interfere with the following phosphorylation reaction.

EXAMPLE 2

5'-O-Dimethoxytrityl-deoxythymidine-3'-[S-(2,4-dichlorobenzyl)-β-cyanoethyl] phosphorothioate (11a)

Method A

To a solution of 1.09 g (2 mmole) of 5'-O-dimethytrityldeoxythymidine and 1 23 g (2.72 mmole) of (9) in 20 ml THF was added simultaneously 2.09 g (3.45 eq) of TPSCl and 0.92ml (0.577 eq) of 1-methylimidazole. The reaction mixture was stirred at r.t. under argon for 2 h, at which time the gummy precipitate was filtered off, the filtrate was evaporated to half of its original volume and then precipitated into hexane. The collected precipitate was purified by flash column chromatography on silica gel (95:5:0.8 $CH_2Cl_2$/MeOH/pyridine) to give 1.48 g of (11a) as a foam. (87%) $^{31}$p-NMR ($CDCl_3$, ppm): 28.0. $^1$H-NMR ($CDCl_3$; δ): 9.10 (br s, 1H, NH), 7.53 (br s, 1H, H$_6$), 7.40–6.80 (m, 16H, ArH), 6.42 (m, 1H, H$_1$'), 5.20 (m, 1H, H$_3$'), 4.15 (m, 5H, H$_4$', $OCH_2$ & $SCH_2$), 3.79 (s, 6H, $OCH_3$), 3.40 (m, 2H, H$_5$'), 2.72–2.30 (m, 4H, $CH_2CN$ & H$_2$'), 1.93 (s, 3H, $CH_3$).

Method B

To compare the above product of Method A prepared by the methods of the invention to a product prepared as per a further procedure a solution of 2.0 g (2.69 mmole) of commercial 5'-O-dimethoxytritylthymidine β-cyanoethyldiisopropyl-3'-phosphoramidite in 10 ml $CH_3CN$ was added to 1.03 ml (1.56 g; 3 eq) of 2,4-dichlorobenzylmercaptane and a solution of 0.473 g (2.5 eq) of tetrazole in 15 ml $CH_3CN$. The reaction mixture was stirred at r.t under argon for 1 h, at which time about 27 ml of 0.1M $I_2$ in THF/pyridine/$H_2O$ (7/2/1; v/v) was added dropwise to this mixture. The resulting solution was added stirred at r.t. for 1 h. Solvent was removed in vacuo and the residue was worked up in the usual manner in EtOAc. The crude product was purified by flash column chromatography on silica gel (9:1 $CH_2Cl_2$/EtOAc→1:1 $CH_2Cl_2$/EtOAc→4:6:0.5 $CH_2Cl_2$/EtOAc/MeOH; all solvent systems contained 1% pyridine) to give 1.76 g of (11a) with a small amount of impurity. (77%).

EXAMPLE 3

N[6]-Benzoyl-5'-O-dimethoxytrityl-deoxycytidine-3-[-S(2,4-dichlorobenzyl)-β-cyanoethyl] phosphorothioate (11b)

Crude (11b) was obtained from 21.8 mmole of N[6]-benzoyl-5'-O-dimethoxytrityl-deoxycytidine by using a similar method to that described for the preparation of (11a). This crude product was purified by flash column chromatography on silica gel (50:35:15:0.7 EtOAc/$CH_2Cl_2$/acetone/pyridine) to give 17.8 g of (11b) as a foam. (87%) $^{31}$p-NMR (CDCl$_3$, ppm): 28.1, 28.0. $^1$H-NMR (CDCl$_3$; δ): 8.75 (br s, 1H, NH), 8.13, 7.88 (2d, 2H, H$_6$ & H$_5$), 7.87–6.80 (m, 21H, ArH), 6.29 (m, 1H, H$_1$'), 5.16 (m, 1H, H$_3$'), 4.38, 4.29 (2m, 1H, H$_4$'), 4.14 (m, 4H, OCH$_2$ & SCH$_2$), 3.80, 3.79 (2s, 6H, OCH$_3$), 3.45 (m, 2H, H$_5$'), 2.92, 2.32 (2m, 2H, H$_2$'), 2.68 (m, 2H, CH$_2$CN).

EXAMPLE 4

5'-O-Dimethoxytrityl-deoxythymidine-3'-[S-(2,4-dichlorobenzyl)] phosphorothioate triethyl ammonium salt (12a)

Crude (12a) (10.1 g; 93%) was obtained from 12 mmole of (11a) by stirring a solution of 11a in 95 ml of CH$_3$CN/Et$_3$N (1/1; v/v) at r.t. for 3 hr. The solvent was removed to give the crude 12a. This crude product was used directly in the subsequent coupling reaction without any further purification. $^{31}$p-NMR (CDCl$_3$, ppm): 17.7. $^1$H-NMR (CDCl$_3$; δ): 8.50 (br s, NH), 7.60 (s, H$_6$), 7.44–6.80 (m, ArH), 6.44 (m, H$_1$'), 5.04 (m, H$_3$'), 4.15 (br s, H$_4$'), 4.00, 3.94 (2s, SCH$_2$), 3.77 (s, OCH$_3$), 3.29 (m, H$_5$'), 3.04 (q, Et$_3$N), 2.60, 2.30 (2m, H$_2$'), 1.30 (m, CH$_3$ & Et$_3$N).

EXAMPLE 5

N[6]-Benzoyl-5'-O-dimethoxytrityl-deoxycytidine-3'-[S(2,4-dichlorobenzyl)] phosphorothioate triethyl ammonium salt (12b)

Crude (12b) (12.01 g; >100%) was obtained from 10.7 mmole of (11b) by using a similar method to that described for the preparation of (12a). $^{31}$p-NMR (CDCl$_3$, ppm): 17.6. $^1$H-NMR (CDCl$_3$; δ): 8.61 (br s, NH), 8.15, 7.88 (2d, H$_6$ & H$_5$), 7.87–6.80 (m, ArH), 6.29 (t, H$_1$'), 4.98 (m, H$_3$'), 4.28 (m, H$_4$'), 4.01, 3.95 (2s, SCH$_2$), 3.78, 3.77 (2s, OCH$_3$), 3.32 (m, H$_5$'), 3.01 (q, Et$_3$N), 2.25 (2m, H$_2$'), 1.30 (t, Et$_3$N).

EXAMPLE 6

Deoxythymidine-3'-[S-(2,4-dichlorobenzyl)-β-cyanoethyl] phosphorothioate (13a)

Crude (13a) was obtained from a solution of 11.4 mmole of (11a) in 20 ml of 3% trichloroacetic acid in CH$_2$Cl$_2$ stirred for 20 mins. The mixture was diluted with CH$_2$Cl$_2$ and the CH$_2$Cl$_2$ layer worked up in the usual manner. This crude product was purified by flash column chromatography on silica gel (6:4 EtOAc/CH$_2$Cl$_2$→EtOAc→9:1 EtOAc/acetone) to give 5.11 g of (13a) as a foam (81%). $^{31}$p-NMR (CDCl$_3$, ppm): 28.8, 28.4. $^1$H-NMR (CDCl$_3$; δ): 9.0 (br s, 1H, NH), 7.46–7.23 (m, 4H, H$_6$ & ArH), 6.14 (2t, J=6.4 Hz, 1H, H$_1$'), 5.20 (m, 1H, H$_3$'), 4.20 (m, 5H, H$_4$', OCH$_2$ & SCH$_2$), 3.85 (m, 2H, H$_5$'), 3.08 (br s, 1H, OH), 2.75 (m, 2H, CH$_2$CN), 2.45 (m, 2H, H$_2$'), 1.92 (s, 3H, CH$_3$).

EXAMPLE 7

N[6]-Benzoyl-deoxycytidine-3'-[S-(2,4-dichlorobenzyl) β-cyanoethyl] phosphorothioate (13b)

A solution of 9.15 g (9.72 mmole) of (11b) in 180 ml of saturated ZnBr$_2$ solution in CH$_2$Cl$_2$/2-propanol (9/1; v/v) was stirred at r.t. for 30 min. The reaction mixture was diluted with CH$_2$Cl$_2$ (sticky and gummy precipitate formed) and saturated NaHCO$_3$ solution. The resulting mixture was stirred and shaken for 20 min. (colorless solid precipitate formed) The mixture was filtered and the remaining orange gumy precipitate was converted to the colorless solid precipitate by trituration with CH$_2$Cl$_2$/saturated NaHCO$_3$ (1/1; v/v) several times. All of the solid precipitate was extracted several times with CH$_2$Cl$_2$/saturated NaHCO$_3$ (1/1; v/v) until tlc showed no more product in the CH$_2$Cl$_2$ layer. The combined CH$_2$Cl$_2$ layers were washed with saturated NaHCO$_3$ once, H$_2$O once and saturated NaCl once. All of the aqueous wash (including saturated NaCl) was back washed with CH$_2$Cl$_2$ twice. The combined CH$_2$Cl$_2$ layers were dried over Na$_2$SO$_4$, filtered and evaporated to give 8.61 g of crude product. The crude product was purified by flash column chromatography on silica gel (60:25:15 EtOAc/CH$_2$Cl$_2$/acetone→56:25:15:4 EtOAc/CH$_2$Cl$_2$/acetone/MeOH) to give 5.33 g of (13b) as a hydroscopic foam. (86%) $^{31}$p-NMR (CDCl$_3$, ppm): 28.6, 28.3. $^1$H-NMR (CDCl$_3$; δ): 8.91 (br s, 1H, NH), 8.25, 7.90 (2d, 2H, H$_6$ & H$_5$), 7.87–7.22 (m, 8H, ArH), 6.21 (t, J=6.4 Hz, 1H, H$_1$'), 5.25 (m, 1H, H$_3$'), 4.32–4.05 (m, 5H, H$_4$', OCH$_2$ & SCH$_2$), 3.94 (br s, 2H, H$_5$'), 3.38 (br s, 1H, OH), 2.73, 2.50 (2m, 4H, CH$_2$CN & H$_2$').

EXAMPLE 8

Preparation of the fully protected TT dimer (14a)

To a solution of 3.15 g (5.73 mmole) of (13a) and 6.69 g (7.43 mmole; 1.3 eq) of (12a) in 60 ml THF was added simultaneously 5.97 g (3.45 eq) of TPSCl and 2.62 ml (0.577 eq) of 1-methylimidazole. The reaction mixture was stirred at r.t. under argon for 2 h, at which time the solid precipitate was filtered off, the filtrate was evaporated to half of its original volume and then precipitated into hexane. The collected precipitate was purified by flash column chromatography on silica gel (5:4:1 EtOAc/CH$_2$Cl$_2$/acetone→9:1 EtOAc/acetone→8:2 EtOAc/acetone; all solvent systems contained 0.5% pyridine) to give 7.28 g of (14a) as a foam. (95%) $^{31}$p-NMR (CDCl$_3$, ppm): 28.9, 28.8, 28.6, 28.5, 28.4, 28.3. $^1$H-NMR (CDCl$_3$; δ): 8.85 (br s, 2H, NH), 7.54 (2 s, 1H, H$_6$), 7.45–6.80 (m, 20H, H$_6$ & ArH), 6.40, 6.15 (2m, 2H, H$_1$'), 5.15 (m, 2H, H$_3$'), 4.30–4.02 (m, 10H, H$_4$', H$_5$', OCH$_2$ & SCH$_2$), 3.78 (s, 6H, OCH$_3$), 3.38 (m, 2H, H$_5$'), 2.72 (m, 2H, CH$_2$CN) 2.55–2.18 (m, 4H, H$_2$'), 1.88, 1.41, 1.38 (3s, 6H, CH$_3$).

EXAMPLE 9

Preparation of the fully protected CC dimer (14b)

Crude (14b) was obtained from 5.5 mmole of (13b) and 7.15 mmole of (12b) by using a similar method to that described for the preparation of (14a). The crude product was purified by flash column chromatography on silica gel (97:3:0.6 CH$_2$Cl$_2$/MeOH/pyridine) to give 7.7 g of (14b) as a foam. (93%) $^{31}$p-NMR (CDCl$_3$, ppm): 29.03, 28.99, 28.77, 28.66, 28.48, 28.39. $^1$H-NMR (CDCl$_3$; δ): 8.75 (br s, 1H, NH), 8.13, 7.88 (2d, 2H, H$_6$ & H$_5$), 7.87–6.80 (m, 21H, ArH), 6.29(m, 1H, H$_1$'), 5.16 (m, 1H, H$_3$'), 4.38, 4.29 (2m, 1H, H$_4$'), 4.14 (m, 4H, OCH$_2$ & SCH$_2$), 3.80, 3.79 (2s, 6H, OCH$_3$), 3.45 (m, 2H, H$_5$'), 2.92, 2.32 (2m, 2H, H$_2$'), 2.68 (m, 2H, CH$_2$CN).

EXAMPLE 10

Preparation of the cyanoethyl-deprotected TT dimer triethyl ammonium salt (15a)

Crude (15a) (7.06 g; 97%) was obtained from 5.28 mmole of (14a) by using a similar method to that described for the preparation of (12a). $^{31}$p-NMR (CDCl$_3$, ppm): 27.78, 27.69, 15.76. $^1$H-NMR (CDCl$_3$; δ): 8.62 (2 br s, NH), 7.55, 7.51, 7.47 (3 s, H$_6$), 7.40–6.80 (m, ArH), 6.39, 6.24 (2m, H$_1$'), 5.21, 4.80 (2m, H$_3$'), 4.30–4.00 (m, H$_4$', H$_5$', OCH$_2$ & SCH$_2$), 3.78 (s, OCH$_3$), 3.37 (m, H$_5$'), 2.91 (q, Et3N), 2.72–1.95 (m, H$_2$') 1.88, 1.37 (2s, CH$_3$), 1.24 (t, Et3N).

EXAMPLE 11

Preparation of the 5' HO-CC dimer (16a)

Crude (16b) was obtained from 4.88 mmole of (14b) by using a similar method to that described for the preparation of (13b). The crude product was purified by flash column chromatography on silica gel (97:3 CH$_2$Cl$_2$/MeOH) to give 5.38 g of (16b) as a foam. (91%) $^{31}$p-NMR (CDCl$_3$, ppm): 29.15, 29.07, 28 99, 28.82, 28.64, 28.48. $^1$H-NMR (CDCl$_3$; δ): 9.01 (br s, 2H, NH), 8.37–7.20 (4 m, 20H, H$_6$, H$_5$ & ArH), 6.18 (m, 2H, H$_1$'), 5.30 (m, 2H, H$_3$'), 4.43–4.12 (m, 10H, H$_4$', H$_5$',OCH$_2$ & SCH$_2$), 3.90 (br s, 2H, H$_5$'), 2.79 (m, 2H, CH$_2$CN), 2.70–1.98 (m, 4H, H$_2$').

EXAMPLE 12

Preparation of fully protected TTCC tetramer (17)

Crude (17) (7.06 g; 97%) was obtained from 3.0 mmole of (16b) and 3.0 mmole of (15a) by using a similar method to that described for the preparation of (14a or 14b). The crude product was purified by flash column chromatography on silica gel (75:23:2:0.7 CH$_2$Cl$_2$/acetone/MeOH/pyridine→95:5:0.7 CH$_2$Cl$_2$/MeOH/pyridine) to give 6.96 g of (17) as a foam. (94%) $^{31}$p-NMR (CDCl$_3$, ppm): 29.49–27.73 (15 peaks). $^1$H-NMR (CDCl$_3$; δ): 9.95, 9.78, 9.70, 9.34 (4br s, 4H, NH), 8.02, 7.90 (2m, 6H, H$_6$ & H$_5$), 7.60–6.80 (m, 35H, ArH), 6.40, 6.20 (2m, 4H, H$_1$'), 5.20 (m, 4H, H$_3$'), 4.47–4.04 (m, 20H, H$_4$', H$_5$', OCH$_2$ & SCH$_2$), 3.78 (s, 6H, OCH$_3$), 3.40 (m, 2H, H$_5$'), 2.90–2.12 (m, 10H, CH$_2$CN & H$_2$'), 1.83, 1.40, 1.38 (3s, 6H, CH$_3$).

EXAMPLE 13

N6-Benzoyl-5'-O-tert-Butoxydiphenylsilyl-2'-Deoxyadenosine-3'-[S-(2,4-dichorobenzyl)-β-Cyanoethyl] Phosphorothioate (18)

A stirred solution of N6-benzoyl-5'-O-tert-butoxydiphenylsilyl-2'-deoxyadenosine (3.32 g, 5.44 mmole) and 15 mL of a 0.512M solution of compound 9 in THF (1.40 equiv) in 55 mL of dry THF was treated with 2,4,6-triisopropylbenzenesulfonyl chloride (5.72 g, 18.89 mmole, 5.76 equiv) at rt under argon. The progress of the reaction was monitored by tlc and $^{31}$p NMR which indicated that the reaction was completed at the end of 2 hr. The insoluble organic salt was filtered off through a Buchner funnel. The organic salt was rinsed twice with 40 mL of THF and the combined filtrate and washing were concentrated at reduced pressure until the whole solution turned milky. The resultant residue was added, dropwise, into 4 L hexanes to solidify the product out from the reaction mixture. The precipitate was collected and purified by flash chromatography eluting with CH$_2$Cl$_2$/MeOH/pyridine (98:2:0.5) to give 2.91 g (58%) of compound 18 as a white foam. $^{31}$p NMR (CDCl$_3$, 81 MHz) δ 28.1 and 27.9 ppm (ratio 45:55); $^1$H NMR (CDCl$_3$, 400 MHz) δ 8.15 ppm (s, H-2 of minor isomer) and 8.14 ppm (s, H-2 of major isomer).

EXAMPLE 14

N6-Benzoyl-5'-O-tert-Butoxydiphenylsilyl-2'-Deoxyadenosine-3'-S-(2,4-dichlorobenzyl) Phosphorothioate (19)

Crude compound 19 will be obtained from compound 18 by using a similar method to that described for the preparation of (12a).

EXAMPLE 15

Preparation of DMTr deprotected 5' HO-TTCC tetramer (20)

The DMT protecting group of compound 17 will be removed to yield crude compound 20 by using a similar method to that described for the preparation of (13a).

EXAMPLE 16

Preparation of the fully protected ATTCC pentamer (21)

Crude compound (19) and compound (20) will be reacted by using a similar method to that described for the preparation of (14a or 14b). The crude product will be purified by flash column chromatography on silica gel (75:23:2:0.7 CH$_2$Cl$_2$/acetone/MeOH/pyridine→95:5:0.7 CH$_2$Cl$_2$/MeOH/pyridine) to give (21) as a foam.

EXAMPLE 17

Preparation of cyanoethyl deprotected DMTr-ATTCC tetramer (22)

The β-cyanoethyl protecting group of compound 21 will be removed to give crude compound 22 from compound 21 by using a similar method to that described for the preparation of (12a).

EXAMPLE 18

Preparation of protected ATTCCG hexamer (23)

Crude (23) will be obtained from (22) and 3'-O-trityl-2'-deoxyguanosine by using a similar method to that described for the preparation of (14a or 14b). The crude product will be purified by flash column chromatography on silica gel (75:23:2:0.7 CH$_2$Cl$_2$/acetone/MeOH/pyridine→95:5:0.7 CH$_2$Cl$_2$/MeOH/pyridine) to give (23) as a foam.

EXAMPLE 19

Preparation of fully deprotected ATTCCG Phosphorothioate hexamer (24)

Compound (23) will be DMTr deprotected utilizing a similar method to that described for the for the preparation of (13a). The crude product from that reaction is then further deprotected by the removal of the S-(2,4-dichlorobenzyl) groups by treatment with thiophenolate in the manner as described by Brill, W. K.-D., Nielsen, J. and Caruthers, M. H. (1991) *J. Am. Chem. Soc.*, 113:3972.

Other Synthetic Methods

EXAMPLE 20

5'-O-Dimethoxytrityl-deoxythymidine-3'(-o-chlorophenyl-β-cyanoethyl) phosphorothioate (25)

To a solution of 1.99 g (2.67 mmole) of commercial 5'-O-dimethoxytrityl-deoxythymidine 3'-phosphoramidite in 10 ml dried and deoxygenated $CH_3CN$ was added 0.83 ml (1.03 g; 3 eq) of 2-chlorophenol and a solution of 0.47 g (2.5 eq) of tetrazole in 15 ml dried and deoxygenated $CH_3CN$. The reaction mixture was stirred at r.t. under argon for 1 h, at which time a solution of $S_8$ (1 g in 9 ml of $CS_2$ and 9 ml of pyridine) was added until the yellow color persisted. The mixture was then stirred at r.t. for 1–2 h. An aliquot of this mixture was withdrawn and analyzed by $^{31}$p-NMR, which indicated that the sulfurization was completed. The reaction mixture was diluted with EtOAc and the sulfur precipitate was removed by filtration. The filtrate was concentrated and the resulting residue was worked up in EtOAc in the usual manner. The crude product was purified by flash column chromatography on silica gel (first 80:20:0.8 $CH_2Cl_2$/EtOAc/pyridine and then 50:50:0.8 $CH_2Cl_2$/EtOAc/pyridine) to give 1.98 g of (25) as a foam. (92%) $^{31}$p-NMR ($CDCl_3$; ppm): 62.9, 62.5. $^1$H-NMR ($CDCl_3$; δ): 9.08, 9.05 (2s, 1H, NH), 7.61, 7.59 (2s, 1H, H$_6$), 7.44–6.80 (m, 17H, ArH), 6.50 (m, 1H, H$_1$'), 5.50 (m, 1H, H$_3$'), 4.39 (m, 3H, H$_4$' & OCH$_2$), 3.79 (s, 6H, OMe), 3.45 (m, 2H, H$_5$'), 2.75 (2t, 2H, CH$_2$CN), 2.66, 2.44 (2m, 2H, H$_2$'), 1.45, 1.43 (2s, 3H, CH$_3$).

EXAMPLE 21

Deoxythymidine-3'(-o-chlorophenyl-β-cyanoethyl) phosphorothioate (26)

A solution of 1.10 g (1.37 mmole) of (25) in 20 ml of 3% trichloroacetic acid in $CH_2Cl_2$ was stirred at r.t. for 30 min. The mixture was diluted with $CH_2Cl_2$ and the $CH_2Cl_2$ layer was worked up in the usual manner. The crude product was purified by flash column chromatography on silica gel (first 1:1 $CH_2Cl_2$/EtOAc and then EtOAc) to give 579 mg pure (26) as a colorless foam. (84%) $^{31}$p-NMR ($CDCl_3$; ppm): 61.3, 61.0. $^1$H-NMR ($CDCl_3$; δ): 8.80 (br s, 1H, NH), 7.45, 7.44 (2s, 1H, H$_6$), 7.37–7.16 (m, 4H, ArH), 6.23 (t, 1H, H$_1$'), 5.41 (m, 1H, H$_3$'), 4.45 (m, 2H, OCH$_2$), 4.33 (m, 1H, H$_4$'), 3.93 (m, 2H, H$_5$'), 2.83 (t, 2H, CH$_2$CN), 2.78 (br s, 1H, OH), 2.58 (m, 2H, H$_2$'), 1.92 (s, 3H, CH$_3$).

EXAMPLE 22

5'-O-Dimethoxytrityl-deoxythymidine-3'(-o-chlorophenyl) phosphorothioate triethyl ammonium salt (27)

A solution of 900 mg (1.12 mmole) of (25) in 9.5 ml of $CH_3CN$/$Et_3N$ (1/1; v/v) was stirred at r.t. for 3 h. Solvent was removed in vacuo to give the crude (27) in a quantitative yield. This crude product was used directly in the coupling reaction without any further purification. $^{31}$p-NMR ($CDCl_3$; ppm): 53.3, 52.5. $^1$H-NMR ($CDCl_3$; δ): 8.52 (br s, NH), 7.65, 7.60 (2s, H$_6$), 7.42–6.76 (m, ArH), 6.48 (m, H$_1$'), 5.60, 5.50 (2m, H$_3$'), 4.41 (m, H$_4$'), 3.78 (s, OCH$_3$), 3.44 (m, H$_5$'), 3.05 (q, Et$_3$N), 2.71, 2.42 (2m, H$_2$'), 1.32 (m, CH$_3$ & Et$_3$N).

EXAMPLE 23

Preparation of the fully protected TT dimer (28)

To a solution of 251 mg (0.5 mmole) of (26) and 491 mg (0.757 mmole: 1.1 eq) of (27) in 9.3 ml THF was added simultaneously 523 mg (3.45 eq) of triisopropylbenzenesulfonyl chloride (TPSCl) and 0.23 ml (0.237 g; 5.77 eq) of 1-methylimidazole. The mixture was stirred at r.t. under argon and the progress of the reaction was monitored by $^{31}$p-NMR and tlc. After 2½ h, the reaction was quenched with 5 ml of pyridine/$H_2O$ (2/1; v/v) and then worked up in the usual manner in $CH_2Cl_2$. The crude product was purified by flash column chromatography on silica gel (95:5:0.8 $CH_2Cl_2$/MeOH/pyridine) to give 330 mg of pure (28) as a colorless foam. (53%) $^{31}$p-NMR ($CDCl_3$; ppm): 62.0, 61.8, 61.7, 61.6, 61.3, 61.2. $^1$H-NMR ($CDCl_3$; δ): 8.85–8.60 (6s, 2H, NH), 7.57 (s, 1H, H$_6$), 7.48–6.81 (m, 22H, H$_6$ & ArH), 6.39 (m, 2H, H$_1$'), 5.50 (m, 2H, H$_3$'), 4.56–4.20 (m, 6H, H$_4$', H$_5$' & OCH$_2$), 3.78 (s, 6H, OCH$_3$), 3.21 (m, 2H, H$_5$'), 2.82 (m, 2H, CH$_2$CN), 2.75–2.28 (m, 4H, H$_2$'), 1.81, 1.42, 1.41 (3s, 6H, CH$_3$).

Those skilled in the art will appreciate that numerous changes and modifications can be made to the preferred embodiments of the invention and that such changes and modifications can be made without departing from the spirit of the invention. It is therefore intended that the appended claims cover all such equivalent variations as fall within the true spirit and scope of the invention.

What is claimed is:

1. The compound S-(2,4-Dichlorobenzyl)-β-cyanoethyl phosphorothioate diester or a salt thereof.

* * * * *